(12) United States Patent
Kaiser et al.

(10) Patent No.: US 11,877,843 B2
(45) Date of Patent: Jan. 23, 2024

(54) HUMAN BODY MEASUREMENT USING THERMOGRAPHIC IMAGES

(71) Applicant: Brainlab AG, Munich (DE)

(72) Inventors: Hagen Kaiser, Munich (DE); Stephen Froehlich, Aschheim (DE); Stefan Vilsmeier, Munich (DE)

(73) Assignee: Brainlab AG, Munich (DE)

( * ) Notice: Subject to any disclaimer, the term of this patent is extended or adjusted under 35 U.S.C. 154(b) by 249 days.

(21) Appl. No.: 16/928,662

(22) Filed: Jul. 14, 2020

(65) Prior Publication Data

US 2020/0337599 A1 Oct. 29, 2020

Related U.S. Application Data

(63) Continuation of application No. 15/528,043, filed as application No. PCT/EP2014/076287 on Dec. 2, 2014, now Pat. No. 10,750,980.

(51) Int. Cl.
*A61B 5/11* (2006.01)
*A61B 5/00* (2006.01)
(Continued)

(52) U.S. Cl.
CPC .......... *A61B 5/1128* (2013.01); *A61B 5/0035* (2013.01); *A61B 5/0064* (2013.01);
(Continued)

(58) Field of Classification Search
None
See application file for complete search history.

(56) References Cited

U.S. PATENT DOCUMENTS

| 6,442,419 | B1 | 8/2002 | Chu et al. |
| 2001/0046316 | A1 | 11/2001 | Miyano et al. |

(Continued)

FOREIGN PATENT DOCUMENTS

| EP | 1657678 | 5/2006 |
| JP | 3253328 | 2/2002 |

(Continued)

OTHER PUBLICATIONS

Amico et al., "Volatile Compounds Detection by IR Acousto-Optic Detectors" J. Byrnes, Unexploded Ordnance Detection and Mitigation (2009) pp. 21-22 (Year: 2009).*

(Continued)

*Primary Examiner* — Bill Thomson
*Assistant Examiner* — Aminah Asghar
(74) *Attorney, Agent, or Firm* — Gray Ice Higdon

(57) ABSTRACT

A medical image processing method performed by a computer, for measuring the spatial location of a point on the surface of a patient's body including: acquiring at least two two-dimensional image datasets, wherein each two-dimensional image dataset represents a two-dimensional image of at least a part of the surface which comprises the point, and wherein the two-dimensional images are taken from different and known viewing directions; determining the pixels in the two-dimensional image datasets which show the point on the surface of the body; and calculating the spatial location of the point from the locations of the determined pixels in the two-dimensional image datasets and the viewing directions of the two-dimensional images; wherein the two-dimensional images are thermographic images.

19 Claims, 2 Drawing Sheets

Figure 1:
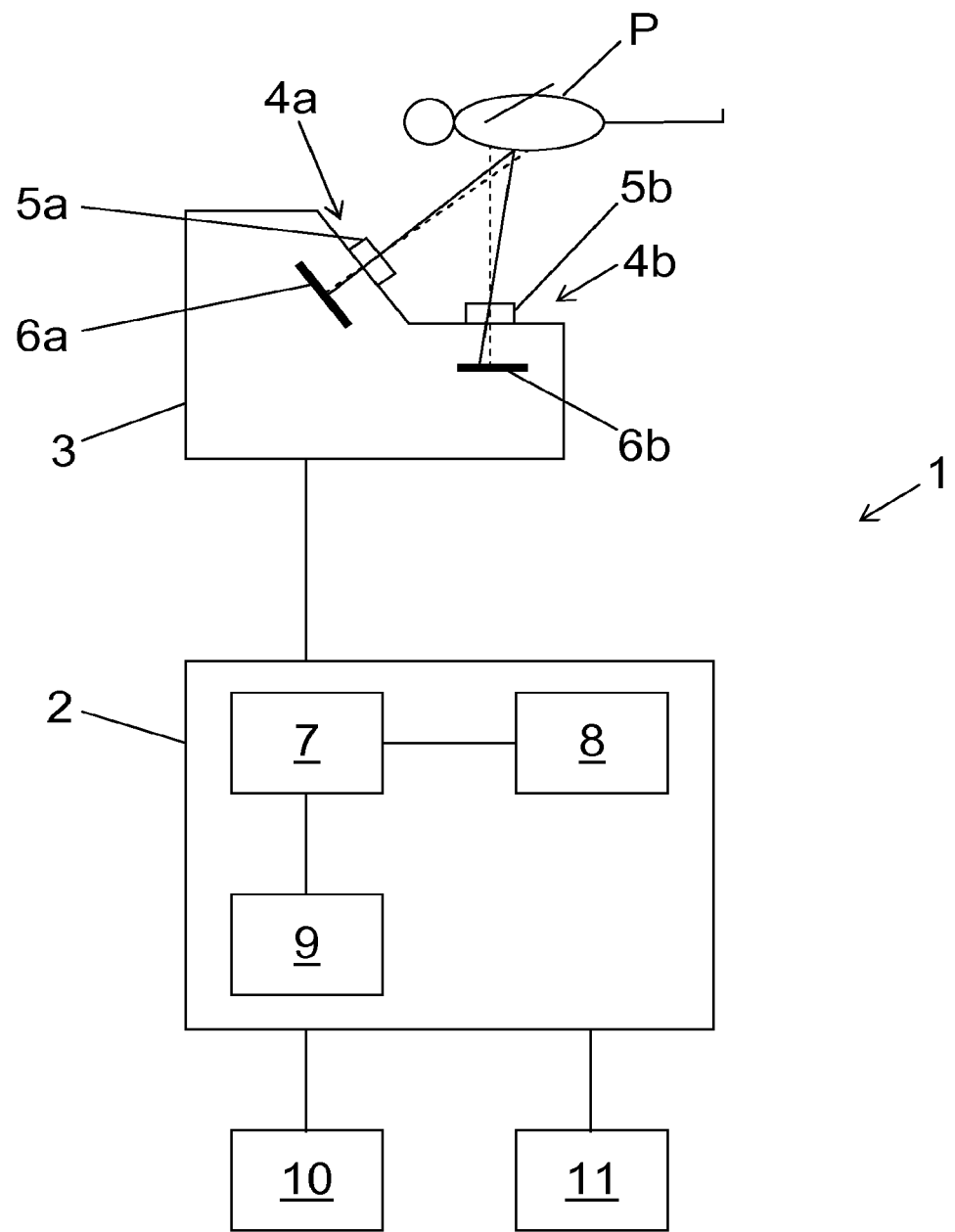

(51) Int. Cl.

| | |
|---|---|
| *A61B 5/113* | (2006.01) |
| *A61B 5/01* | (2006.01) |
| *G01J 5/00* | (2022.01) |
| *G06T 7/33* | (2017.01) |
| *H04N 13/204* | (2018.01) |
| *A61N 5/10* | (2006.01) |
| *A61B 5/055* | (2006.01) |
| *G03B 35/02* | (2021.01) |
| *G06T 7/70* | (2017.01) |
| *A61B 6/03* | (2006.01) |
| *A61B 6/00* | (2006.01) |
| *G06T 7/00* | (2017.01) |
| *H04N 13/00* | (2018.01) |
| *H04N 13/239* | (2018.01) |
| *G01R 33/48* | (2006.01) |
| *G01J 5/48* | (2022.01) |
| *G01J 5/10* | (2006.01) |

(52) U.S. Cl.
CPC ............ *A61B 5/0077* (2013.01); *A61B 5/015* (2013.01); *A61B 5/055* (2013.01); *A61B 5/11* (2013.01); *A61B 5/113* (2013.01); *A61B 5/7292* (2013.01); *A61B 6/032* (2013.01); *A61B 6/5247* (2013.01); *A61N 5/1049* (2013.01); *A61N 5/1068* (2013.01); *G01J 5/00* (2013.01); *G03B 35/02* (2013.01); *G06T 7/0012* (2013.01); *G06T 7/33* (2017.01); *G06T 7/70* (2017.01); *H04N 13/204* (2018.05); *A61B 2560/0223* (2013.01); *A61B 2576/00* (2013.01); *A61B 2576/02* (2013.01); *A61N 5/1069* (2013.01); *G01J 5/10* (2013.01); *G01J 5/48* (2013.01); *G01J 2005/0077* (2013.01); *G01R 33/4808* (2013.01); *G06T 2207/10004* (2013.01); *G06T 2207/10028* (2013.01); *G06T 2207/10048* (2013.01); *G06T 2207/10081* (2013.01); *G06T 2207/10088* (2013.01); *G06T 2207/30196* (2013.01); *H04N 13/239* (2018.05); *H04N 2013/0081* (2013.01)

(56) References Cited

U.S. PATENT DOCUMENTS

| | | | |
|---|---|---|---|
| 2007/0051889 | A1 | 3/2007 | Yannacone et al. |
| 2011/0021944 | A1 | 1/2011 | Arnon et al. |
| 2012/0008741 | A1 | 1/2012 | Hendriks et al. |
| 2013/0235163 | A1 | 9/2013 | Joo |
| 2014/0267758 | A1 | 9/2014 | Neff et al. |
| 2014/0307074 | A1 | 10/2014 | Ryabov et al. |
| 2016/0135729 | A1* | 5/2016 | Mestha .................. A61B 5/748 600/408 |
| 2016/0150966 | A1* | 6/2016 | Heinrich ............... A61B 5/1114 600/476 |

FOREIGN PATENT DOCUMENTS

| | | |
|---|---|---|
| KR | 20140001766 | 1/2014 |
| WO | 2016086976 | 6/2016 |

OTHER PUBLICATIONS

Krotosky et al., "On Color-,Infrared-, and Multimodal-Stereo Approaches to Pedestrian Detection", IEEE Transactions on Intelligent Transportation Systems, IEEE, Piscataway, NJ, USA. vol. 8, No. 4, Dec. 1, 2007 (Dec. 1, 2007), pp. 619-629, XP011197257, ISSN: 1524-9050, DOI: 10.1109/ TITS.2007.908722. sections III.-VI.

European Search Report issued for Application No. 2020324.8-1115 dated Feb. 4, 2021.

Amico et al., "Volatile Compounds Detection by IR Acousto-Optic Detectors" J. Byrnes, Unexploded Ordnance Detection and Mitigation (2009) pp. 21-22. 2009.

International Search Report and Written Opinion, PCT/EP2014/076287 dated Sep. 9, 2015, dated Sep. 9, 2015.

Hartley, et al. "Multiple View Geometry in Computer Vision". Cambridge University Press. Second Edition. 2004. 2004.

Scharstein, et al. "High-Accuracy Stereo Depth Maps Using Structured Light". IEE Computer Society Conference on Computer Vision and Pattern Recognition (CVPR 2003), vol. 1, pp. 195-202, Jun. 2003. Jun. 2003.

Mei, et al. "On building an accurate stereo matching system on graphics hardware".

* cited by examiner

HUMAN BODY MEASUREMENT USING THERMOGRAPHIC IMAGES

The present invention relates to: a medical data processing method performed by a computer; a computer program and system for measuring the spatial location of a point on the surface of a patient's body; and related methods, computer programs and systems.

Many medical applications require knowledge of the spatial location of a point on the surface of a patient's body. The location is for example given in two-dimensional or three-dimensional space and is for example represented by two-dimensional or three-dimensional co-ordinates. One possible approach is to analyse a stereoscopic image of the patient's body in order to determine the spatial locations of one or more points on the body's surface. A stereoscopic image is typically obtained by capturing two or more two-dimensional images from different and known viewing directions. In this document, the expression "different viewing directions" encompasses both non-parallel viewing directions and parallel but non-identical viewing directions. A viewing direction is typically defined by an optical axis of a camera which is used to capture a two-dimensional image.

The two-dimensional images are then analysed in order to find the pixel in each of the images which shows the same point on the surface of the body. The spatial location of the point can be calculated from the locations of the pixels in the two-dimensional images and the optical properties of the cameras. Examples of this approach are for example described in R. Hartley and A. Zisserman, "Multiple View Geometry in Computer Vision", Cambridge University Press, $2^{nd}$ edition, 2003 and in X. Mei, X. Sun, M. Zhou, S. Jiao, H. Wang, and X. Zhang, "On building an accurate stereo matching system on graphics hardware", GPUCV 2011.

An improved method for measuring the spatial location of a point on the surface of a patient's body, a computer and a system are disclosed in the independent claims. Advantageous embodiments, including other methods which involve the method of the independent claim, are disclosed in the dependent claims.

One aspect of the present invention relates to a medical data processing method, performed by a computer, for measuring the spatial location of a point on the surface of a patient's body. The method involves the step of acquiring at least two two-dimensional image datasets, wherein each two-dimensional image dataset represents a two-dimensional image of at least a part of the surface which comprises the point, and wherein the two-dimensional images are taken from different and known viewing directions. As explained above, different viewing directions can be non-parallel or parallel but non-identical viewing directions.

A two-dimensional image dataset is for example acquired from a data storage or a camera. A camera comprises a lens system which images at least the part of the surface which comprises the point onto a sensor which converts radiation emitted from the point into image data. The properties of the lens system, such as its focal length and any distortions caused by the lens system, are preferably known to the method. Optionally, the distortions are corrected within the camera before the method acquires the two-dimensional image dataset from the camera. The output of the camera can be stored in the data storage and subsequently acquired from the data storage.

The method may also involve the step of determining the pixels in the two-dimensional image datasets which show said point on the surface of the body. This means that one pixel is identified in each two-dimensional image, wherein the identified pixels show the same point. The positions of the identified pixels in the respective two-dimensional images depend on the location of the imaged point in space. Pixels showing the same point are also referred to as corresponding pixels. Many algorithms for determining corresponding pixels in a set of two-dimensional images are known within the field of image processing. Determining the pixels for example involves determining the location of the pixels in the two-dimensional image datasets. If the two-dimensional image datasets are structured as two-dimensional arrays of pixels, then the location of a pixel is typically given as a pair of co-ordinates which define a position in the array.

The method may further involve the step of calculating the spatial location of the point from the locations of the determined pixels in the two-dimensional image datasets and the viewing directions of the two-dimensional images. Depending on how it is implemented, this step can also involve calculating the spatial location from the properties of the lens systems of the cameras used to capture the two-dimensional image datasets. Many algorithms for calculating the spatial location of a point from a set of two-dimensional images are known within the field of image processing. One simple approach is to determine a straight line in space on which the point lies, for each of the two-dimensional image datasets, from the imaging properties of the respective camera and the position of the respective pixel of the corresponding pixels in the two-dimensional image. The spatial location is then calculated as the point in space at which the straight lines corresponding to the two-dimensional image datasets intersect.

The spatial location of the point is for example given in a reference co-ordinate system. This reference co-ordinate system can be a global co-ordinate system, such as an Earth-relative co-ordinate system, or a co-ordinate system defined with respect to a room in which the cameras are located, or a co-ordinate system which is defined with respect to the cameras.

In accordance with one aspect of the present invention, the two-dimensional images are thermographic images. In a thermographic image, the pixels do not represent the colour of a point in the visible spectrum, but rather a temperature or temperature distribution emitted from the point. Since each point emits a range of temperatures up to a maximum temperature, a pixel of a thermoscopic image can for example represent this maximum temperature of the point. In this document, a thermographic image preferably only represents the thermal radiation emitted from the surface of the patient's body in a non-visible spectrum. A thermographic image can only be effectively presented to a human eye if frequency mapping is performed. This is often referred to as false-colour representation.

The advantage of using thermographic images to measure the spatial location of a point is that the spectrum of the thermal radiation is independent of ambient conditions, such as illumination, and the optical properties of the surface, so even if a large area of the surface has the same optical properties in the visual spectrum, it may exhibit a particular pattern in its thermal radiation, such that corresponding points in the set of two-dimensional image datasets can be found more easily and more reliably.

In known approaches using two-dimensional images in the visible spectrum, the problem of uniform areas has been addressed by projecting a characteristic optical pattern onto the surface. Corresponding points can then be found using this known optical pattern. However, if the patient's body, and therefore the surface, moves relative to the projector emitting the optical pattern, a particular point of this pattern does not illuminate the same point on the surface over time. By contrast, the thermal pattern irradiated by a patient's body moves together with the body relative to the cameras, such that a relative movement between the cameras and the patient's body can be reliably determined.

In one embodiment, the spatial locations of a plurality of points on the surface of the body are measured. This preferably involves utilising the same two-dimensional image datasets for all points in the plurality of points, but determining the pixels in the two-dimensional image datasets and calculating the spatial location for each of the points in the plurality of points. The position of the surface of the patient's body can be determined from the spatial locations of a plurality of points, such as for example three or more points. In this document, the term "position" means the spatial location in up to three translational dimensions and/or the rotational alignment in up to three rotational dimensions.

In one embodiment, the method comprises the step of discarding points which have spatial locations outside a predefined spatial range. In this step, a kind of spatial filtering is thus implemented. In this case, points outside a region of interest can be discarded. This can be advantageous if the surface comprises two sub-surfaces which can move relative to each other. It is then possible to discard points which do not lie on one of the sub-surfaces, such that the remaining points can be more reliably registered to another dataset, because the discarded points, which can move relative to the remaining points, are ignored for the purpose of registration.

The method can for example comprise the step of filtering the two-dimensional image datasets in order to discard pixels which represent wavelengths outside a predefined wavelength range. In one example of this, pixels which represent wavelengths corresponding to temperatures below 20° C., 25° C. or 30° C. are discarded. This has the advantage that pixels which do not belong to the surface of the patient's body can for example be removed from the two-dimensional image datasets. This step is preferably performed before the step of determining the pixels in the two-dimensional image datasets which show the point on the surface of the body, such that the filtering step reduces the computational effort involved in the determining step.

By combining spatial filtering and temperature selection, it is possible to robustly decide whether a pixel is part of the surface of the patient's body or not.

In one embodiment, the thermographic two-dimensional images represent wavelengths between 8 μm and 14 μm. This range corresponds to typical temperatures for the surface of a patient's body. The thermographic two-dimensional images preferably do not represent wavelengths in the near infrared spectrum. The near infrared spectrum is typically understood to extend as far as wavelengths of 2.5 μm or 3 μm.

In one embodiment, the method comprises the step of assigning a descriptor to the point on the surface of the patient's body. A descriptor is for example a value which is calculated from the properties of the point and optionally also from the properties of points in the vicinity of the point. A descriptor is typically used to unambiguously identify a point. In this document, a descriptor can also be a set of descriptors or descriptor values. A descriptor is for example calculated from the two-dimensional image datasets, for example from the properties of a pixel which represents the point on the surface and/or from the properties of pixels in the vicinity of this pixel.

One advantage of the descriptor is that it is basically invariant for similar viewing directions (such as viewing directions which form an angle of for example 1°, 2°, 5° or) 10° or over time (such as for example for 1 second, 2 seconds, 5 seconds, 10 seconds, 15 seconds, 30 seconds, 60 seconds or even longer). This means that the descriptor can advantageously be used to identify pixels which show the same point on the surface of the body in two-dimensional image datasets taken from different viewing directions and/or at different points in time.

The principles of calculating a descriptor are for example disclosed in M. Calonder, V. Lepetit, M. Özuysal, T. Trzcinski, C. Strecha, P. Fua, "BRIEF: Computing a Local Binary Descriptor Very Fast", IEEE Transactions on Pattern Analysis and Machine Intelligence, Volume 34, issue No. 07, July 2012, pages 1281 to 1298, which is incorporated by this reference.

In one aspect, the present invention also relates to a medical data processing method for determining the alignment between a patient and a three-dimensional dataset which represents at least a part of a contour of the patient's body. The patient's body has a surface, and the shape of the surface is the contour of the patient's body. The shape of the surface can be represented by the locations of points on the surface, wherein the more points are measured, the more accurately the shape is represented.

This method involves the step of acquiring the three-dimensional dataset. The three-dimensional dataset can for example represent the contour by means of a set of points on the contour of the patient's body, such as a set of points created by measuring the spatial locations of a plurality of points on the surface of a patient's body, as described above. In another implementation, the three-dimensional dataset can for example represent the contour by means of a three-dimensional image which shows the contour. The contour is for example indicated by sufficiently different values of adjacent voxels of the three-dimensional image. The three-dimensional image can be obtained by using any suitable imaging technique, such as for example magnetic resonance imaging or computed tomography.

Typically, a dataset co-ordinate system is at least implicitly assigned to the three-dimensional dataset. This dataset co-ordinate system can be an internal co-ordinate system, such as a co-ordinate system with axes representing the dimensions of a three-dimensional array of voxels, such as for example a medical 3D image. The dataset co-ordinate system can alternatively be an external co-ordinate system, such as the reference co-ordinate system. This is for example the case if the three-dimensional dataset was acquired by using a medical imaging apparatus which was at a known position in the reference co-ordinate system. If the three-dimensional dataset represents a set of points, then the dataset co-ordinate system is for example a Cartesian co-ordinate system with a defined point of origin, and the three-dimensional dataset represents the locations of the points relative to this point of origin.

The three-dimensional dataset is typically obtained by measuring the contour of the patient's body. At the time of measurement, the patient's body exhibits a particular spatial position. The three-dimensional dataset therefore also exhibits a particular (virtual) spatial position at this point. The spatial position of the three-dimensional dataset is for example represented by the spatial position of the dataset co-ordinate system.

The method may also involve measuring the locations of a plurality of points on the surface of the body, as described above. The time at which the locations of the plurality of points are measured is preferably later than the time at which the three-dimensional dataset was created.

There are thus two representations of the surface of the patient's body, one provided by the three-dimensional dataset and one provided by the locations of the plurality of points on the surface. If the shape of the patient's body has not changed between the time the three-dimensional dataset was created and the time the locations of the plurality of points were measured, then the contour as represented by the three-dimensional dataset will be exactly equal to the shape of the surface as described by the locations of the plurality of points.

The method may also comprise the step of calculating alignment information which represents a virtual relative position between the three-dimensional dataset and the locations of the plurality of points, such that the measured locations of the plurality of points lie on the contour of the body as represented by the three-dimensional dataset. The algorithm used for this calculation depends on the nature of the three-dimensional dataset, for example on whether the three-dimensional dataset is a three-dimensional image or a set of points. This is also known as registration, and suitable algorithms are known to the person skilled in the art.

The virtual relative position can for example describe the relative position between the dataset co-ordinate system and a reference co-ordinate system for which the contour represented by the three-dimensional dataset matches the surface of the patient's body as described by the spatial locations of the points. The difference between this virtual relative position and the actual relative position between the two co-ordinate systems represents the alignment, which can also be referred to as a displacement, between the actual position of the surface and the (virtual) position of the contour as represented by the three-dimensional dataset.

The method can for example comprise the additional step of calculating movement control data from the alignment information. In one example, the movement control data describe how the patient's body has to be moved within the reference co-ordinate system in order for the surface of the patient's body to match the contour of the patient's body as represented by the three-dimensional dataset. This is for example useful for moving the patient's body into a position which is identical to its position at the time the three-dimensional dataset was created. One example application for this is radiotherapy, in which the patient's body has to be moved to a predetermined position relative to a linac (linear particle accelerator). If the three-dimensional dataset—which is assumed to have a particular position in the reference co-ordinate system, for example when it was created using a medical imaging apparatus which was at a known position in the reference co-ordinate system—represents the predetermined position of the patient's body in the reference co-ordinate system, then the movement control data can be used to correctly align the patient's body in the reference co-ordinate system, for example relative to the linac.

Conversely, the movement control data can describe how the three-dimensional dataset has to be positioned in the reference co-ordinate system in order for it to represent the actual position of the patient's body in the reference co-ordinate system. This is advantageous for image-guided procedures, in particular if medical instruments are tracked relative to the reference co-ordinate system and an image of the medical instrument is to be displayed together with the three-dimensional dataset.

A further embodiment of the present invention also relates to a medical data processing method for verifying the position of at least a part of a patient's body. This method involves the step of acquiring a three-dimensional dataset which represents at least a part of a contour of the part of the patient's body in a target position of the part of the patient's body. The target position is for example defined with respect to the reference co-ordinate system and is for example a target position relative to a medical apparatus such as a linac.

The method may also comprise the step of measuring the locations of a plurality of points on the surface of the body, as described above. There are thus two representations of the patient's body, namely a three-dimensional dataset representing the contour of the patient's body which describes the target position of the patient's body, and the locations of the plurality of points which represent the actual position of the patient's body.

The method may further comprise the step of determining whether or not the locations of the plurality of points lie on the contour of the part of the patient's body as represented by the three-dimensional dataset. In other words, a determination is made as to whether or not the actual position of the patient's body matches the target position of the patient's body.

As in the method for virtually aligning a patient's body and the three-dimensional dataset, the three-dimensional dataset can be a three-dimensional image dataset, such as a CT or an MR image dataset, of at least a part of the patient's body which comprises the part of the contour of the body.

As in the method for virtually aligning a patient's body and the three-dimensional dataset, the three-dimensional dataset can be a dataset which represents spatial locations of a plurality of points on the part of the contour of the patient's body which were measured, as described above.

It should be noted that the expressions "contour" and "surface" are occasionally used in this document for brevity and are to be understood to mean "at least a part of the contour" and "at least a part of the surface", respectively.

The present invention also relates to a medical data processing method for tracking at least a part of the surface of a patient's body. In this document, the word "tracking" means determining the position at different points in time.

This method comprises the step of measuring first locations of a plurality of points on the surface of the body, as explained above, at a first point in time and measuring second locations of the plurality of points, as explained above, at a second point in time which is later than the first point in time. This means that the locations of the same plurality of points are measured at two different points in time.

The method also comprises the step of calculating a movement of at least the part of the surface of the body from the difference between the first locations and the second locations. This movement is preferably represented by movement data. The movement is for example a translation in up to three translational dimensions and/or a rotation in up to three rotational dimensions.

The present invention also relates to a medical data processing method for determining a patient's vital signs. Vital signs measure basic functions of a body such as heartbeat or respiration.

This method comprises the step of measuring the location of at least one point, which is referred to as a tracked point, on the surface of the body, as described above, at different points in time. It is assumed that the movement of this point over time represents the basic function of the body which is to be monitored.

The method also comprises the step of calculating the patient's vital signs from the measured locations of the tracked point over time. The algorithm used in this calculating step depends on the nature of the vital signs to be determined. Suitable algorithms for different kinds of vital signs are known to the person skilled in the art.

The present invention also relates to a computer program embodied on a non-transitory computer-readable medium which, when running on a computer or loaded onto a computer, causes the computer to perform any one or more of the data processing methods described above.

The present invention also relates to a system for measuring the spatial location of a point on the surface of a patient's body, comprising: at least two imaging units for recording two-dimensional thermographic images of at least a part of the surface which comprises the point, wherein the two-dimensional thermographic images are represented by two-dimensional image datasets and the imaging units are arranged such that the two-dimensional images are taken from different and known viewing directions; and a computer on which the program described above is stored and/or run.

The invention relates to the Applicant's product ExacTrac which is used for patient setup and monitoring in radiotherapy. ExacTrac currently utilises a marker-based IR tracking system in combination with a stereoscopic X-ray system. While the X-ray system is very precise, it can only be used to take snapshots of the position of the patient's body at well-defined points in time during the treatment. Otherwise, the patient would be exposed to unjustifiable levels of radiation. The marker-based IR system is used to monitor the patient in real time. In order to track the position of the patient's body, markers have to be attached either directly to the patient's body or to fixation devices which fix the patient in a certain position.

Preparing each patient is time-consuming and can therefore reduce the number of patients who can be treated per day. Markers can become dirty and may have to be serviced or even replaced. Fixation devices are generally considered uncomfortable for patients. Depending on the severity of the patient's illness, treatments may have to be interrupted if for example the patient's very restricted freedom of movement cause mental stress or even pain.

These problems can be successfully tackled by using a marker-less tracking device as shown in the present invention. Using this system, it is possible to dispense with fixation devices and markers, and the position of the patient's body can still be tracked precisely in real time. Unlike other marker-less tracking devices, the present application allows for monitoring at much higher frame rates, since a far smaller quantity of data has to be computed as compared to typical structured light systems. There is also no need to synchronise separate systems, such as for example a projector and a camera.

Unlike a purely video-based approach, such as is currently used in academic research, the present invention is independent of lighting conditions and/or reflections, which serves to stabilise the tracking results. In hospitals, for example, the lights in the treatment room are often dimmed in order to aid the patient in remaining calm during treatment.

Within the framework of the invention, computer program elements can be embodied by hardware and/or software (this includes firmware, resident software, micro-code, etc.).

Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a technical and in particular tangible device.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, in particular volumetric CBCT), X-ray tomography, magnetic resonance tomography (MRT or MRI), conventional X-ray, sonography and/or ultrasound examinations, and positron emission tomography. The image data thus generated are also referred to as "medical imaging data". Analytical devices in particular are used to generate the image data in apparatus-based imaging methods. The imaging methods are in particular used for medical diagnostics, to analyse the anatomical body in order to generate images which are described by the image data. The imaging methods are also in particular used to detect pathological changes in the human body. However, some of the changes in the anatomical structure, in particular the pathological changes in the structures (tissue), may not be detectable and in particular may not be visible in the images generated by the imaging methods. A tumour represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernible in the image generated by the imaging method. In addition to these tumours, referred to as "enhancing" tumours, it is thought that approximately 10% of brain tumours are not discernible on a scan and are in particular not visible to a user looking at the images generated by the imaging method.

The method in accordance with the invention is a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer for example comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the World Wide Web (WWW) and located in a so-called cloud of computers which are all connected to the World Wide Web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (or World Wide Web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer may comprise interfaces in order to receive or output data and/or perform an analogue-to-digital conversion. The data are for example data which represent physical properties and/or which are generated from technical signals. The technical signals are typically generated by means of (technical) detection devices (such as for example devices for detecting marker devices) and/or (technical) analytical devices (such as for example devices for performing imaging methods), wherein the technical signals are typically electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display which is operatively coupled to the computer for receiving display control data from the computer in order to generate signals which are then used to display image information content on the display device. A specific embodiment of such a computer monitor is a digital light box. The monitor can also be the monitor of a portable, in particular handheld device such as a smart phone or personal digital assistant or digital media player.

The expression "acquiring data" encompasses (within the framework of a data processing method) the scenario in which the data are determined by the data processing method or program. Determining data encompasses measuring physical quantities and transforming the measured values into data, in particular digital data, and/or computing the data by means of a computer and in particular within the framework of the method in accordance with the invention. The meaning of "acquiring data" also encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

As mentioned, the invention does not involve or in particular comprise or encompass an invasive step which would represent a substantial physical interference with the body requiring professional medical expertise to be carried out and entailing a substantial health risk even when carried out with the required professional care and expertise. In particular, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

In the following, the invention is described with reference to the enclosed figures which represent preferred embodiments of the invention. The scope of the invention is not however limited to the specific features disclosed in the figures.

FIG. 1 schematically shows a system for measuring the spatial location of a point on the surface of a patient's body.

Figure 2:
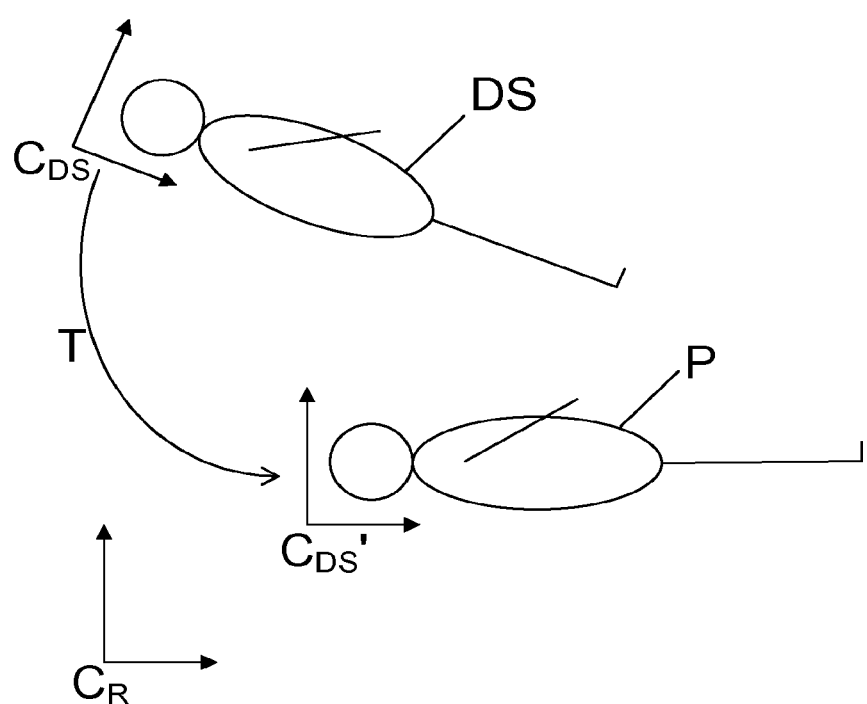

FIG. 2 schematically shows an example of virtually aligning a patient and a three-dimensional dataset.

FIG. 1 shows a system 1 for measuring the spatial location of a point on the surface of the body of a patient P. The system 1 essentially comprises a computer 2 and a stereoscopic thermographic camera 3. The computer 2 is connected to an input device 10, such as a keyboard or a mouse, and to an output device 11 such as a monitor.

The stereoscopic thermographic camera 3 comprises two thermographic imaging units 4a and 4b. The imaging unit 4a comprises a lens system 5a and a sensor 6a. The imaging unit 4b correspondingly comprises a lens system 5b and a sensor 6b. The lens systems 5a and 5b guide incident thermal radiation onto the sensors 6a and 6b, respectively, wherein each of the sensors 6a and 6b creates a two-dimensional thermographic image which preferably represents wavelengths of between 8 μm and 14 μm. The lens systems 5a and 5b have characteristic axes similar to the optical axis of a camera which captures an image in the visible spectrum. As can be seen from FIG. 1, the two imaging units 4a and 4b have different characteristic axes and therefore different viewing directions. The characteristic axes are shown as dashed lines in FIG. 1.

Thermal radiation emitted from a point on the body is guided onto corresponding pixels of the sensors 6a and 6b in accordance with the spatial location of the point on the surface of the patient's body and the characteristics of the lens systems 5a and 5b.

In the present example, the sensors 6a and 6b are two-dimensional arrays of sensor cells which convert incident thermal radiation into a voltage which corresponds to the temperature of the corresponding point on the surface of the patient's body. The temperature is typically derived from the wavelength of the maximum within the spectrum of the incident infrared radiation.

The computer 2 comprises a central processing unit 7, a memory unit 8 and an interface 9. The memory unit 8 stores program data and/or working data, such as the image datasets acquired from the stereoscopic camera 3. The computer is connected to the input device 10, the output device 11 and/or the stereoscopic camera 3 via an interface 9.

The computer 2 acquires the two two-dimensional image datasets, which were captured using the sensors 6a and 6b, from the stereoscopic camera 3. The computer 2 is provided with the properties of the stereoscopic camera 3, such that for each pixel in each of the two-dimensional thermographic image datasets, the computer 2 knows or is able to calculate the line on which points imaged by said pixel are located.

The computer 2 determines the pixels in the two two-dimensional thermal images which capture the thermal radiation emitted from the same point on the surface of the patient's body. The pixels are for example determined by means of a descriptor which describes the thermal signature of the point and the area surrounding this point, such that the descriptor is characteristic of this point.

For each of the two-dimensional cameras 4a and 4b, the computer 2 uses the position of the determined pixel in the two-dimensional thermographic image and the properties of the lens system 5a or 5b, respectively, to determine the line in space on which the point on the surface of the patient's body lies. These lines are shown as solid lines in FIG. 1. The computer 2 then calculates the point in space at which the two lines intersect each other. The location of this point is the location of the point on the surface of the patient's body.

If the computer 2 measures the spatial locations of a plurality of points on the surface of the patient's body, a set of points is obtained which represents the shape of the surface of the patient's body.

One advantage of using thermographic images rather than images in the visible spectrum is that the thermal signature of the body is independent of the optical characteristics of the surface of the patient's body and/or the characteristics of the light which is emitted onto the patient's body.

FIG. 2 shows the principle of aligning the patient P and a three-dimensional dataset which represents at least a part of a contour of the body of the patient P. In this embodiment, the three-dimensional dataset represents a medical three-dimensional image such as an MR or CT image. The three-dimensional dataset comprises a three-dimensional array of voxels. The contour of the patient's body can be derived from the values of the voxels.

FIG. 2 shows the body of the patient P in a reference co-ordinate system $C_R$. The computer 2 then measures the spatial locations of a plurality of points on the surface of the patient's body in the reference co-ordinate system $C_R$. The position of the stereoscopic camera 3 in the reference co-ordinate system $C_R$ is known, such that the computer 2 can measure the spatial locations of the points in this reference co-ordinate system $C_R$.

In order to make the example easier to understand, FIG. 2 shows the surface of the body of the patient P rather than the points on the surface of the patient's body. FIG. 2 also shows the contour of the patient's body as represented by the three-dimensional dataset DS. A dataset co-ordinate system $C_{DS}$ is assigned to the three-dimensional dataset DS. The position of the contour as shown in FIG. 2 corresponds to the position of the patient's body when the three-dimensional dataset DS was captured.

The computer 2 calculates alignment information which represents a relative position between the three-dimensional dataset DS and the locations of the plurality of points on the surface of the patient's body, such that the locations of the plurality of points lie on the contour of the patient's body as represented by the three-dimensional dataset DS. The alignment information describes the position of the dataset co-ordinate system $C_{DS}$ in the reference co-ordinate system $C_R$, such that the contour represented by the three-dimensional dataset DS matches the surface of the patient's body as represented by the measured spatial locations of the points on the surface of the patient's body. This position of the dataset co-ordinate system $C_{DS}$ is shown as the co-ordinate system $C_{DS}'$ in FIG. 2.

If the dataset co-ordinate system $C_{DS}$ has a particular initial position in the reference co-ordinate system $C_R$, for example if the three-dimensional dataset DS was created by a medical imaging device which was at a known position in the reference co-ordinate system $C_R$, then a transformation T can be calculated in order to align the three-dimensional dataset DS with the actual position of the patient's body, i.e. to register the dataset DS to the patient P. Once the three-dimensional dataset DS is aligned with the patient's body, the three-dimensional dataset DS can be displayed on the display device 11, for example together with an image of a medical instrument which is tracked in the reference co-ordinate system $C_R$, for example by a known medical tracking system.

Conversely, if the initial position of the dataset co-ordinate system $C_{DS}$ corresponds to a target position of the patient's body in the reference co-ordinate system $C_R$, then the inverse of the transformation T describes how the actual position of the patient's body in the reference co-ordinate system $C_R$ needs to be changed so as to match the target position. One application of this is in order to move the patient P into the position which is equal to the position in which the three-dimensional dataset DS was created.

The invention claimed is:

1. A computer implemented method for tracking at least a part of a surface of a patient's body, comprising:
   measuring, by one or more processors, at a first point in time, first locations of a plurality of points on the surface of the patient's body by acquiring at least two two-dimensional image datasets,
      wherein each two-dimensional image dataset represents a thermographic two-dimensional image of at least the part of the surface of the patient's body which comprises the plurality of points, and
      wherein the two-dimensional thermographic images are taken from different and known viewing directions;
   assigning, by the one or more processors, a descriptor to each of at least one point, of the plurality of points on the surface of the patient's body, wherein the descriptor for each of the at least one point describes a thermal signature, of a corresponding point, that is characteristic of the corresponding point for identifying the corresponding point;
   for each of the at least one point:
      determining, by the one or more processors and using at least the assigned descriptors that respectively describe a thermal signature for each of the at least one point of the plurality of points on the surface of the patient's body, a first and a second pixels, respectively in one of the two two-dimensional image datasets which show the plurality of points on the surface of the patient's body, wherein the first pixel and the second pixel both correspond to a respective point of the at least one point, and
      calculating, by the one or more processors, a spatial location of the respective point of the at least one point of the plurality of points from corresponding locations of the determined first and second pixels in the two-dimensional image datasets and the viewing directions of the two-dimensional thermographic images;
   measuring, by the one or more processors, at a second point in time which is later than the first point in time, second locations of the at least one point of the plurality of points in the same manner as the first locations; and
   calculating, by the one or more processors, a movement of at least the part of the surface of the body from the difference between the first locations and the second locations.

2. The method of claim 1, further comprising discarding, by the one or more processors, at least one of the plurality of points which have spatial locations outside a predefined spatial range.

3. The method of claim 1, further comprising filtering, by the one or more processors, the two-dimensional image datasets in order to discard pixels which represent wavelengths outside a predefined wavelength range.

4. The method of claim 1 wherein the two-dimensional thermographic images represent wavelengths between 8 μm and 14 μm.

5. The method of claim 1, wherein the thermal signature of the corresponding point is independent of optical characteristics of the surface of the patient's body.

6. The method of claim 1, wherein the thermal signature of the corresponding point is independent of light emitted onto the patient's body.

7. The method of claim 1, wherein the spatial location of the respective point is in three translational dimensions.

8. A non-transitory computer-readable program storage medium comprising instructions which, when executed by at least one processor, causes the at least one processor to track at least a part of a surface of a body of a patient, the at least one processor executing the steps of:
   measuring, at a first point in time, first locations of a plurality of points on the surface of the body of the patient by acquiring at least two two-dimensional image datasets, wherein each two-dimensional image dataset represents a thermographic two-dimensional image of at least the part of the surface of the patient's body which comprises the plurality of points, and wherein the two-dimensional thermographic images are taken from different and known viewing directions;
   assigning a descriptor to each of at least one point in the plurality of points, the descriptor for each of the at least one point including a calculated value from thermal properties of a corresponding point of the at least one point and also thermal properties of further points in a vicinity of the corresponding point of the at least one point wherein the calculated value from the thermal properties of the corresponding point is characteristic of the corresponding point for identifying the corresponding point;

for each of the at least one point:
determining a first and a second pixels respectively in one of the two-dimensional image datasets which show said plurality of points on the surface of the body of the patient using at least one of the assigned descriptors, wherein the first pixel is in one of the two two-dimensional image datasets and corresponds to a respective point of the at least one point, and wherein the second pixel is in a different one of the two two-dimensional image datasets and corresponds to the respective point of the at least one point, calculating a spatial location of the respective point of the at least one point of the plurality of points from corresponding locations of the determined first and second pixels in the two-dimensional image datasets and the viewing directions of the two-dimensional thermographic images;

measuring, at a second point in time which is later than the first point in time, second locations of the at least one point of the plurality of points in the same manner as the first locations; and calculating a movement of at least the part of the surface of the body of the patient from the difference between the first locations and the second locations.

9. The non-transitory computer-readable program storage medium of claim 8, further comprising instructions which, when executed by the at least one processor, causes the at least one processor to execute a step of:

discarding, by the one or more processors, at least one of the plurality of points which have spatial locations outside a predefined spatial range.

10. The non-transitory computer-readable program storage medium of claim 8, further comprising instructions which, when executed by the at least one processor, causes the at least one processor to execute a step of:

filtering, by the one or more processors, the two-dimensional image datasets in order to discard pixels which represent wavelengths outside a predefined wavelength range.

11. The non-transitory computer-readable program storage medium of claim 8, wherein the two-dimensional thermographic images represent wavelengths between 8 µm and 14 µm.

12. The non-transitory computer-readable program storage medium of claim 8, wherein the thermal signature of the corresponding point is independent of optical characteristics of the surface of the patient's body.

13. The non-transitory computer-readable program storage medium of claim 8, wherein the spatial location of the respective point is in three translational dimensions.

14. A system including a non-transitory memory and one or more processors operable to execute instructions stored in the non-transitory memory, comprising instructions to:

measure, at a first point in time, first locations of a plurality of points on the surface of the patient's body by acquiring at least two two-dimensional image datasets, wherein each two-dimensional image dataset represents a thermographic two-dimensional image of at least the part of the surface of the patient's body which comprises the plurality of points, and wherein the two-dimensional thermographic images are taken from different and known viewing directions;

assign a descriptor to each of at least one point, of the plurality of points on the surface of the patient's body, wherein the descriptor for each of the at least one point describes a thermal signature, of a corresponding point, that is characteristic of the corresponding point for identifying the corresponding point;

for each of the at least one point:
determine, using at least the assigned descriptors that respectively describe a thermal signature for each of the at least one point of the plurality of points on the surface of the patient's body, a first and a second pixels, respectively in one of the two two-dimensional image datasets which show the plurality of points on the surface of the patient's body, wherein the first pixel is in one of the two two-dimensional image datasets and corresponds to the respective point of the at least one point, and wherein the second pixel is in a different one of the two two-dimensional image datasets and corresponds the respective point of the at least one point, and calculate a spatial location of the respective point of the at least one point of the plurality of points from corresponding locations of the determined first and second pixels in the two-dimensional image datasets and the viewing directions of the two-dimensional thermographic images;

measure at a second point in time which is later than the first point in time, second locations of the at least one point of the plurality of points in the same manner as the first locations; and calculate a movement of at least the part of the surface of the body from the difference between the first locations and the second locations.

15. The system of claim 14, wherein the one or more processors are further operable to:

discard at least one of the plurality of points which have spatial locations outside a predefined spatial range.

16. The system of claim 15, wherein the one or more processors are further operable to:

filter the two-dimensional image datasets in order to discard pixels which represent wavelengths outside a predefined wavelength range.

17. The system of claim 15, wherein the two-dimensional thermographic images represent wavelengths between 8 µm and 14 µm.

18. The system of claim 15, wherein the thermal signature of the corresponding point is independent of optical characteristics of the surface of the patient's body.

19. The system of claim 15, wherein the thermal signature of the corresponding point is independent of light emitted onto the patient's body.

* * * * *

UNITED STATES PATENT AND TRADEMARK OFFICE
CERTIFICATE OF CORRECTION

| | | |
|---|---|---|
| PATENT NO. | : 11,877,843 B2 | |
| APPLICATION NO. | : 16/928662 | |
| DATED | : January 23, 2024 | |
| INVENTOR(S) | : Hagen Kaiser et al. | |

It is certified that error appears in the above-identified patent and that said Letters Patent is hereby corrected as shown below:

On the Title Page

Item (54), and in the Specification, Column 1, Line 1-2, delete "HUMAN BODY MEASUREMENT USING THERMOGRAPHIC IMAGES" and insert -- Tracking a Part of a Surface of a Patient's Body Using Thermographic Images --, therefor.

In the Specification

In Column 4, Line 6, after "or" delete ")".

In Column 4, Line 7, after "10°" insert -- ) --.

In the Claims

In Column 14, Claim 4, Line 39, after "claim 1" insert -- , --.

In Column 15, Claim 8, Line 3, after "point" insert -- , --.

In Column 16, Claim 14, Line 2, delete "the surface" and insert -- a surface --, therefor.

In Column 16, Claim 14, Line 2, delete "the patient's" and insert -- a patient's --, therefor.

In Column 16, Claim 14, Line 6, delete "the part" and insert -- a part --, therefor.

In Column 16, Claim 16, Line 46, delete "15" and insert -- 14 --, therefor.

In Column 16, Claim 17, Line 51, delete "15" and insert -- 14 --, therefor.

Signed and Sealed this
Twelfth Day of March, 2024

Katherine Kelly Vidal
*Director of the United States Patent and Trademark Office*

In Column 16, Claim 18, Line 54, delete "15" and insert -- 14 --, therefor.

In Column 16, Claim 19, Line 57, delete "15" and insert -- 14 --, therefor.